(12) United States Patent
Schneider et al.

(10) Patent No.: US 11,866,400 B2
(45) Date of Patent: *Jan. 9, 2024

(54) PROCESS FOR HYDROFORMYLATION OF OLEFINS USING PT AND DPEPHOS

(71) Applicant: EVONIK OPERATIONS GMBH, Essen (DE)

(72) Inventors: Carolin Schneider, Monheim am Rhein (DE); Ralf Jackstell, Rostock (DE); Matthias Beller, Ostseebad Nienhagen (DE); Robert Franke, Marl (DE)

(73) Assignee: EVONIK OPERATIONS GMBH, Essen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 18/064,950

(22) Filed: Dec. 13, 2022

(65) Prior Publication Data

US 2023/0192584 A1 Jun. 22, 2023

(30) Foreign Application Priority Data

Dec. 17, 2021 (EP) .................................. 21215368

(51) Int. Cl.
*C07C 45/50* (2006.01)
*B01J 23/42* (2006.01)

(52) U.S. Cl.
CPC ........ *C07C 45/505* (2013.01); *C07C 2523/42* (2013.01)

(58) Field of Classification Search
CPC .................................................... C07C 45/505
See application file for complete search history.

(56) References Cited

U.S. PATENT DOCUMENTS 7,217,828 B2 5/2007 Selent et al.
9,206,105 B2 12/2015 Christiansen et al.

OTHER PUBLICATIONS

European Search Report dated Jun. 17, 2022 for European Patent Application No. 21215368.8 (5 pages in German with English Translation).
Meessen, P. et al. Highly regioselective hydroformylation of internal, functionalized olefins applying Pt Sn complexes with large bite angle diphosphines. Journal of Organometallic Chemistry. 1998. vol. 551, No. 1-2, pp. 165-170.
U.S. Appl. No. 18/064,945, Schneider et al., filed Dec. 13, 2022.
U.S. Appl. No. 18/064,946, Schneider et al., filed Dec. 13, 2022.
U.S. Appl. No. 18/064,947, Schneider et al., filed Dec. 13, 2022.
U.S. Appl. No. 18/064,948, Schneider et al., filed Dec. 13, 2022.
U.S. Appl. No. 18/064,949, Schneider et al., filed Dec. 13, 2022.
U.S. Appl. No. 18/064,952, Schneider et al., filed Dec. 13, 2022.
U.S. Appl. No. 18/064,953, Schneider et al., filed Dec. 13, 2022.
U.S. Appl. No. 18/064,955, Schneider et al., filed Dec. 13, 2022.
U.S. Appl. No. 18/064,958, Schneider et al., filed Dec. 13, 2022.
Examination Report dated Oct. 16, 2023 in Saudi Arabia Patent Application No. 122440827 (7 pages in Arabic; 5 pages English translation).

*Primary Examiner* — Sikarl A Witherspoon
(74) *Attorney, Agent, or Firm* — Smith, Gambrell & Russell, LLP

(57) ABSTRACT

Process for hydroformylation of olefins using Pt and DPEphos.

15 Claims, No Drawings

PROCESS FOR HYDROFORMYLATION OF OLEFINS USING PT AND DPEPHOS

The present invention relates to a process for hydroformylation of olefins using Pt and DPEphos.

P. Meessen et al., Journal of Organometallic Chemistry, 551, (1998), 165-170 describes the use of DPEphosPtCl$_2$ for the hydroformylation of methyl 3-pentenoate.

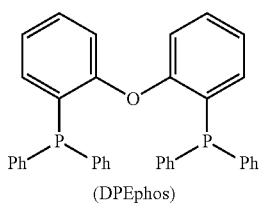

(DPEphos)

The problem addressed by the present invention is that of providing a novel hydroformylation process. The process here is to afford an increased yield compared to the process known from the prior art.

This object is achieved by a process according to claim 1.

Process comprising the process steps of:
a) initially charging an olefin;
b) adding a compound of formula (I):

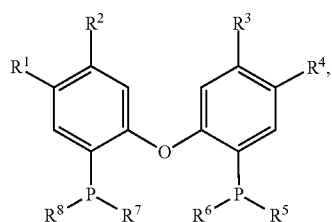

(I)

where R$^1$, R$^2$, R$^3$, R$^4$, R$^5$, R$^6$, R$^7$, R$^8$ are selected from: —H, —(C$_1$-C$_{12}$)-alkyl, —(C$_6$-C$_{20}$)-aryl, and at least two of the R$^5$, R$^6$, R$^7$, R$^8$ radicals are —(C$_6$-C$_{20}$)-aryl;
c) adding a Pt compound capable of forming a complex;
d) adding a bromine compound or an iodine compound;
e) feeding in CO and H$_2$;
f) heating the reaction mixture from steps a) to e), to convert the olefin to an aldehyde.

In this process, process steps a) to e) can be effected in any desired sequence. Typically, however, CO and H$_2$ are added after the co-reactants have been initially charged in steps a) to d).

It is possible here for process steps c) and d) to be effected in one step by adding PtBr$_2$ or PtI$_2$.

In a preferred variant of the process, the Pt compound and the bromine compound or iodine compound are added in one step by adding PtBr$_2$ or PtI$_2$.

The expression (C$_1$-C$_{12}$)-alkyl encompasses straight-chain and branched alkyl groups having 1 to 12 carbon atoms. These are preferably (C$_1$-C$_8$)-alkyl groups, more preferably (C$_1$-C$_6$)-alkyl, most preferably (C$_1$-C$_4$)-alkyl.

Suitable (C$_1$-C$_{12}$)-alkyl groups are especially methyl, ethyl, propyl, isopropyl, n-butyl, iso-butyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,1-dimethylbutyl, 1,2-dimethylbutyl, 2,2-dimethylbutyl, 1,3-dimethylbutyl, 2,3-di methylbutyl, 3,3-di methylbutyl, 1,1,2-trimethylpropyl, 1,2,2-trimethylpropyl, 1-ethylbutyl, 1-ethyl-2-methylpropyl, n-heptyl, 2-heptyl, 3-heptyl, 2-ethylpentyl, 1-propylbutyl, n-octyl, 2-ethylhexyl, 2-propylheptyl, nonyl, decyl.

The expression (C$_6$-C$_{20}$-aryl encompasses mono- or polycyclic aromatic hydrocarbyl radicals having 6 to 20 carbon atoms. These are preferably (C$_6$-C$_{14}$)-aryl, more preferably (C$_6$-C$_{10}$)-aryl.

Suitable (C$_6$-C$_{20}$)-aryl groups are especially phenyl, naphthyl, indenyl, fluorenyl, anthracenyl, phenanthrenyl, naphthacenyl, chrysenyl, pyrenyl, coronenyl. Preferred (C$_6$-C$_{20}$-aryl groups are phenyl, naphthyl and anthracenyl.

In one variant of the process, R$^5$, R$^6$, R$^7$, R$^8$ are —(C$_6$-C$_{20}$-aryl.

In one variant of the process, R$^5$, R$^6$, R$^7$, R$^8$ are -Ph.

In one variant of the process, R$^1$ and R$^4$ are —H.

In one variant of the process, R$^2$ and R$^3$ are —H.

In one variant of the process, the compound of formula (I) has the structure (1):

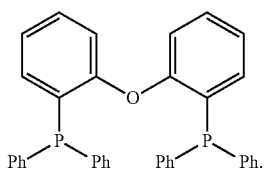

(1)

In one variant of the process, the Pt compound is selected from: Pt(II)I$_2$, Pt(II)Br$_2$, Pt(IV)I$_4$, Pt(IV)Br$_4$, diphenyl(1,5-COD)Pt(II), Pt(II)(acac)$_2$, Pt(0)(PPh$_3$)$_4$, Pt(0)(DVTS) solution (CAS:68478-92-2), Pt(0)(ethylene)(PPh$_3$)$_2$, Pt(II)Br$_2$(COD), tris(benzylideneacetone)Pt(0), Pt(II)(OAC)$_2$ solution, Pt(O)(t-Bu)$_2$, Pt(II)(COD)Me$_2$, Pt(II)(COD)I$_2$, Pt(IV)IMe$_3$, Pt(II)(hexafluoroacetylacetonate)$_2$.

In one variant of the process, the Pt compound is selected from: Pt(II)I$_2$, Pt(II)Br$_2$.

In one variant of the process, the iodine compound or the bromine compound is selected from: alkali metal halide, alkaline earth metal halide, NH4X, alkylammonium halide, dialkyl halide, trialkyl halide, tetraalkyl halide, cycloalkylammonium halide.

In one variant of the process, a bromine compound which is Pt(II)Br2 is added in process step d).

In one variant of the process, the bromine compound is added in an amount in the range of 0.1 to 10, measured in equivalents based on Pt.

In one variant of the process, an iodine compound which is Pt(II)I$_2$ is added in process step d).

In one variant of the process, the iodine compound is added in an amount in the range of 0.1 to 10, measured in equivalents based on Pt.

In one variant of the process, this process comprises the additional process step e'): e') adding a solvent.

In one variant of the process, the solvent is selected from: THF, DCM, ACN, heptane, DMF, toluene, texanol, pentane, hexane, octane, isooctane, decane, dodecane, cyclohexane, benzene, xylene, Marlotherm, propylene carbonate, MTBE, diglyme, triglyme, diethyl ether, dioxane, isopropanol, tert-butanol, isononanol, isobutanol, isopentanol, ethyl acetate.

In one variant of the process, the solvent is selected from: THF, DCM, ACN, heptane, DMF, toluene, texanol.

In one variant of the process, CO and $H_2$ are fed in at a pressure in a range from 1 MPa (10 bar) to 6 MPa (60 bar).

In one variant of the process, CO and $H_2$ are fed in at a pressure in a range from 1 MPa (20 bar) to 6 MPa (50 bar).

In one variant of the process, the reaction mixture is heated to a temperature in the range from 25° C. to 150° C.

In one variant of the process, the reaction mixture is heated to a temperature in the range from 30° C. to 130° C.

In one variant of the process, the olefin is selected from: ethene, propene, 1-butene, cis- and/or trans-2-butene, isobutene, 1,3-butadiene, 1-pentene, cis- and/or trans-2-pentene, 2-methyl-1-butene, 3-methyl-1-butene, 2-methyl-2-butene, hexene, tetramethylethylene, heptene, 1-octene, 2-octene, di-n-butene, or mixtures thereof.

The invention is to be illustrated in more detail hereinafter by a working example.

Experimental Description

A vial was charged with $PtX_2$ (X=halogen), ligand, and an oven-dried stirrer bar. The vial is then sealed with a septum (PTFE-coated styrene-butadiene rubber) and phenolic resin cap. The vial is evacuated and refilled with argon three times. Toluene and 1-octene were added to the vial using a syringe. The vial was placed in an alloy plate, which was transferred to an autoclave of the 4560 series from Parr Instruments under an argon atmosphere. After purging the autoclave three times with $CO/H_2$, the synthesis gas pressure was increased to 40 bar at room temperature. The reaction was conducted at 120° C. for 20 h. On termination of the reaction, the autoclave was cooled to room temperature and cautiously decompressed. Yield and selectivity were determined by GC analysis.

Hydroformylation of 1-octene

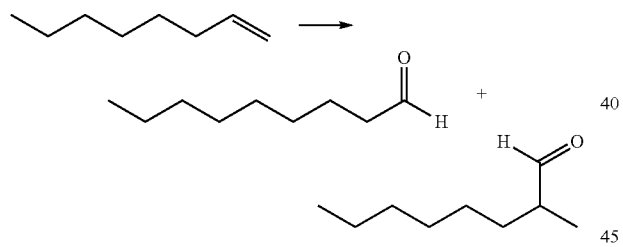

Reaction Conditions:

10.0 mmol of 1-octene, 0.1 mol % $PtX_2$, 2.2 equivalents of ligand, solvent: toluene, $p(CO/H_2)$: 40 bar, T: 120° C., t: 20 h.

Yields:

| Ligand | Halogen | Yield [%] |
|---|---|---|
| 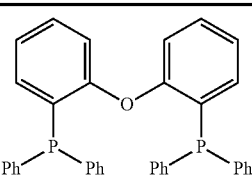 | I/Br/Cl | 76/45/14 |

As the experimental results show, the object is achieved by the process according to the invention.

The invention claimed is:

1. A process comprising the process steps of:
    a) initially charging an olefin;
    b) adding a compound of formula (I):

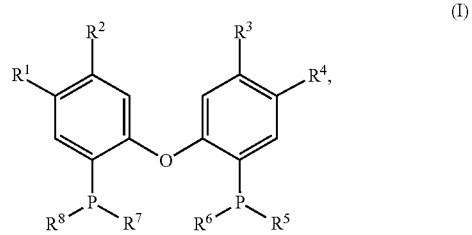

where $R^1$, $R^2$, $R^3$, $R^4$, $R^5$, $R^6$, $R^7$ and $R^8$ are selected from: —H, —($C_1$-$C_{12}$)-alkyl or, —($C_6$-$C_{20}$)-aryl, and at least two of the $R^5$, $R^6$, $R^7$, $R^8$ radicals are —($C_6$-$C_{20}$)-aryl;
    c) adding a Pt compound capable of forming a complex;
    d) adding a bromine compound or an iodine compound;
    e) feeding in CO and $H_2$;
    f) heating the reaction mixture from steps a) to e), to convert the olefin to an aldehyde.

2. The process according to claim 1, where $R^5$, $R^6$, $R^7$ and $R^8$ are —($C_6$-$C_{20}$)-aryl.

3. The process according to claim 1, where $R^5$, $R^6$, $R^7$ and $R^8$ are -Ph.

4. The process according to claim 1, where $R^1$ and $R^4$ are —H.

5. The process according to claim 1, where $R^2$ and $R^3$ are —H.

6. The process according to claim 1, wherein the compound of formula (I) has the structure (1):

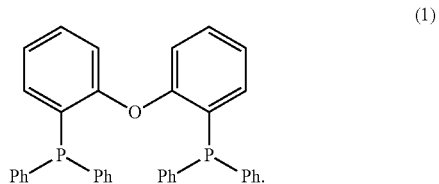 [SMILES: c1ccc(P(c2ccccc2)c2ccccc2Oc2ccccc2P(c2ccccc2)c2ccccc2)cc1]

7. Process according to claim 1, wherein the Pt compound is selected from: $Pt(II)I_2$, $Pt(II)Br_2$, $Pt(IV)I_4$, $Pt(IV)Br_4$, diphenyl(1,5-COD)Pt(II), $Pt(II)(acac)_2$, $Pt(0)(PPh_3)_4$, Pt(0) (DVTS) solution (CAS:68478-92-2), $Pt(0)(ethylene)(PPh_3)_2$, $Pt(II)Br_2(COD)$, tris(benzylideneacetone)Pt(0), $Pt(II)(OAC)_2$ solution, $Pt(0)(t-Bu)_2$, $Pt(II)(COD)Me_2$, $Pt(II)(COD)I_2$, $Pt(IV)IMe_3$ or $Pt(II)(hexafluoroacetylacetonate)_2$.

8. The process according to claim 1, wherein a bromine compound which is $Pt(II)Br_2$ is added in process step d).

9. The process according to claim 8, wherein the bromine compound is added in an amount in the range of 0.1 to 10, measured in equivalents based on Pt.

10. The process according to claim 1, wherein in process step d) an iodine compound is added, which is $Pt(II)I_2$.

11. The process according to claim 10, wherein the iodine compound is added in an amount in the range of 0.1 to 10, measured in equivalents based on Pt.

12. The process according to claim 1, comprising the additional process step e'):
    e') adding a solvent.

13. The process according to claim 12, wherein the solvent is selected from: THF, DCM, ACN, heptane, DMF, toluene, texanol, pentane, hexane, octane, isooctane, decane, dodecane, cyclohexane, benzene, xylene, propylene carbonate, MTBE, diglyme, triglyme, diethyl ether, dioxane, isopropanol, tert-butanol, isononanol, isobutanol, isopentanol, ethyl acetate.

14. The process according to claim 1, wherein CO and $H_2$ are fed in at a pressure in a range from 1 MPa (10 bar) to 6 MPa (60 bar).

15. The process according to claim 1, wherein the reaction mixture is heated to a temperature in the range from 25° C. to 150° C.

* * * * *